(12) United States Patent
Jutila

(10) Patent No.: US 7,661,429 B2
(45) Date of Patent: Feb. 16, 2010

(54) PLUNGER

(75) Inventor: Ilkka Jutila, Vanhalinna (FI)

(73) Assignee: Bayer Schering Pharma Oy, Turku (FI)

( * ) Notice: Subject to any disclaimer, the term of this patent is extended or adjusted under 35 U.S.C. 154(b) by 415 days.

(21) Appl. No.: 10/579,207

(22) PCT Filed: Nov. 17, 2004

(86) PCT No.: PCT/FI2004/000688

§ 371 (c)(1),
(2), (4) Date: May 12, 2006

(87) PCT Pub. No.: WO2005/048893

PCT Pub. Date: Jun. 2, 2005

(65) Prior Publication Data

US 2007/0129734 A1    Jun. 7, 2007

(30) Foreign Application Priority Data

Nov. 19, 2003    (FI)    ................................. 20031679

(51) Int. Cl.
*A61F 6/06* (2006.01)
*A61F 6/14* (2006.01)
*A61B 17/42* (2006.01)

(52) U.S. Cl. .................. 128/840; 606/119; 128/839

(58) Field of Classification Search .............. 606/119, 606/201, 99, 108, 141, 216, 916; 128/840, 128/838, 839; 600/201, 33, 34, 35; D24/133, D24/141; 604/15, 16, 17, 18; 29/280
See application file for complete search history.

(56) References Cited

U.S. PATENT DOCUMENTS 2,338,135 A * 1/1944 Schmitz, Jr. ................. 128/838
3,777,748 A * 12/1973 Abramson ................... 128/840
3,783,861 A * 1/1974 Abramson ................... 128/840
3,910,445 A * 10/1975 Garza et al. ................. 215/328
3,918,444 A    11/1975 Hoff et al. .................... 128/130
3,918,445 A * 11/1975 Okamoto et al. ............ 128/840

(Continued)

FOREIGN PATENT DOCUMENTS

DE    25 06 890    5/1976

(Continued)

*Primary Examiner*—Patricia Bianco
*Assistant Examiner*—Victoria Hicks
(74) *Attorney, Agent, or Firm*—James C. Lydon

(57) ABSTRACT

A plunger intended for an inserter for an intrauterine device with a T-body, which plunger has a first end and a second end. The plunger's length in its longitudinal direction is substantially larger than the diameter of the cross-section perpendicular to the longitudinal direction. The plunger's cross-section is substantially circular. An opening (17) has been arranged in the plunger's longitudinal direction so that the opening's longitudinal axis is substantially the same as the plunger's longitudinal axis. The opening at the first end of the plunger is arranged to expand in a direction perpendicular to its longitudinal axis to form a tip portion, so that the tip portion has at least one surface (6, 7, 8, 9, 10, 11), which along at least a portion of the tip portion's length turns at least 35° in relation to a first plane in parallel with the longitudinal axis and at least 35° in relation to a plane at an angle in relation to the longitudinal axis.

10 Claims, 6 Drawing Sheets

U.S. PATENT DOCUMENTS

| | | | | |
|---|---|---|---|---|
| 4,143,656 | A | * | 3/1979 | Holmes ........................ 128/840 |
| 4,372,302 | A | * | 2/1983 | Akerlund .................... 128/840 |
| 4,959,067 | A | * | 9/1990 | Muller ........................ 606/190 |
| 5,785,053 | A | * | 7/1998 | Macandrew et al. ........ 128/840 |
| D442,688 | S | * | 5/2001 | DeWeerd ................... D24/141 |
| D497,990 | S | * | 11/2004 | Jutila ......................... D24/114 |

FOREIGN PATENT DOCUMENTS

| | | |
|---|---|---|
| DE | 42 37 950 | 8/1994 |
| EP | 0 948 948 | 10/1999 |

* cited by examiner

PLUNGER

FIELD OF THE INVENTION

The object of the invention is an arrangement at the tip of the plunger of an inserter. Particularly, the invention relates to a plunger intended for an inserter for an intrauterine device with a T-body, which plunger has a first end and a second end as well as a first dimension, which is the longitudinal direction of the plunger, and the length of which plunger in its longitudinal direction is substantially larger than the diameter of the cross-section perpendicular to the longitudinal direction, and the cross-section of which plunger is substantially circular, and through which an opening has been arranged in its longitudinal direction so that the longitudinal axis of the opening is substantially the same as the longitudinal axis of the plunger.

BACKGROUND OF THE INVENTION

In known inserters, for instance in inserters used to position intrauterine devices, the devices are usually adapted to be arranged within the plunger of the inserter by pulling them into place through the tip of the inserter and the plunger. Then the tip must be designed so that the device can be pulled within the inserter without damaging the device.

Typical intrauterine devices have a so-called T-body with a body part and two branch portions, whereby a metal spiral or a hormone capsule is arranged in the body. The end of the body part further has a loop with a string attached to it, with which the device can be pulled into the plunger and removed from the uterus after use. The device is typically pulled into the plunger with this loop in front, whereby it is important that the plunger directs the device into the plunger in the correct position, i.e. without damaging the loop (and the rest of the body).

If the device is pulled into the plunger in a wrong position, the tip edges of the inserter or the plunger can damage the edges of the loop. If the pulling is continued and the device does not turn into the correct position, the string will finally cut through the loop of the T-body. The edges of a damaged loop can also cause the loop and thus the device to get jammed within the inserter or plunger.

For instance, in an inserter according to the prior art intended for the positioning of intrauterine devices the tip portion of the plunger is shaped so that it turns the T-body of the device into the correct position from an angle of about 30°, and in 50% of the cases also from an angle of 60°. A structure of this kind is shown in the enclosed FIG. 1 and in the patent FI 97946.

OBJECTS OF THE INVENTION

The object of the invention is to provide a plunger of an inserter solving the problems mentioned above. Thus, an object of the invention is particularly to provide a plunger of an inserter with a tip structure, which enables the positioning of the device within the plunger so that the probability of damage to the device is as low as possible.

DESCRIPTION OF THE INVENTION

The objects of the invention are attained as presented in the enclosed claims.

The object of the invention is a plunger intended for an inserter for an intrauterine device with a T-body, which plunger has a first end and a second end, and a first dimension, which is the longitudinal direction of the plunger, and the length of which plunger in its longitudinal direction is substantially larger than the diameter of the cross-section perpendicular to the longitudinal direction, and the cross-section of which plunger is substantially-circular, and through which plunger an opening has been arranged in its longitudinal direction so that the longitudinal axis of the opening is substantially the same as the longitudinal axis of the plunger.

The body of an inserter according to the invention is characterised in that the opening at the first end of the plunger is arranged to expand in a direction perpendicular to the direction of the longitudinal axis to form a tip portion, so that the tip portion has at least one surface, which along at least a portion of the length of the tip portion turns at least 35° in relation to a first plane in parallel with the longitudinal axis and at least 35° in relation to a plane being at an angle in relation to the longitudinal axis.

Thus, the plunger of the inserter according to the invention has in the tip portion an arrangement which facilitates the device to be put into the inserter so that damage to the device is substantially less probable than in prior art inserters. For instance, when intrauterine devices with T-body are put into the plunger, the tip of the plunger will turn the T-body into the correct position from error angles, which are substantially larger than at present.

With the aid of models it has been found that the tip structure of the plunger will turn a T-body into the correct position even from angles of 90°.

The at least one surface of the tip portion means a surface, which does not have any abrupt discontinuities, such as for instance a sharp angle of 90° angle.

According to an embodiment of the invention said plane being at an angle in relation to the longitudinal axis is perpendicular to said direction of the longitudinal axis. According to another embodiment of the invention said at least one surface turns 90° in relation to the first plane and 90° in relation to the plane being at an angle.

The tip of the plunger according to the invention can have one or more surfaces. There can be for instance two, three, four, five, six, seven, eight, nine, ten or twelve surfaces.

In a plunger according to the invention said surfaces can also form surface pairs.

According to one embodiment of the invention there are two of said surfaces, and they can form a surface pair so that the surfaces forming the surface pair are mirror images of each other in relation to a second plane in parallel with the longitudinal axis, which second plane is perpendicular to said first plane.

According to another embodiment of the invention there are four of said surfaces, and they can form two surface pairs, which are mirror images of each other in relation to said first plane in parallel with the longitudinal axis. In addition, at least the surfaces forming a surface pair in the second surface pair can be mirror images of each other in relation to a second plane in parallel with the longitudinal axis, which second plane is perpendicular to said first plane. In both surface pairs the surfaces forming the surface pairs are advantageously mirror images of each other in relation to said plane.

In all embodiments the surface pairs may be connected with each other, in other words, the tip structure does not necessarily comprise any right angles or other points of discontinuity. It is also possible that the surface pairs are not connected with each other, as presented below in connection with the Figures.

However, according to one embodiment presented below in connection with the drawing the tip structure can also contain right angles.

A plunger according to the invention can further have at least one surface, which is substantially in parallel with said first plane.

According to one embodiment of the invention a surface or one of the surfaces will turn substantially 90° in relation to both planes. Of course it is also possible that two or three of said surfaces turn substantially 90° in relation to both planes, whereby the other surfaces turn in an amount corresponding to some other degree, for instance 45°, 60°, 70° or 82°. If the two surfaces forming a surface pair turn 45° or generally substantially less than 90°, a kind of sharp angle is created at the joint between them.

According to an embodiment of the invention a surface or one of the surfaces will turn substantially 90° in relation to at least one of said planes. According to one embodiment all surfaces turn substantially 90° in relation to both said planes. However, to a person skilled in the art it is obvious that the surfaces can turn also for instance 50°, 60°, 65°, 70°, 75°, 82°, 87°, 89°, 91° or 92°.

Said surfaces, or one or more of them, can along the whole length of the tip portion be substantially in parallel with the direction of the plane of the cross-section of the plunger. The plane of the cross-section of the plunger is that plane, which is perpendicular to the longitudinal axis of the plunger. Said surfaces, or one or more of them, can along the length of the tip portion also have different directions than the direction of the plane of the cross-section of the plunger, they can, in other words, be inclined in relation to it. It is obvious that also all combinations are possible, in other words, that the different surfaces can have different directions along the length of the tip portion.

The invention is described in more detail in the enclosed Figures, which are non-limiting.

SHORT DESCRIPTION OF THE DRAWING

Figure 5:
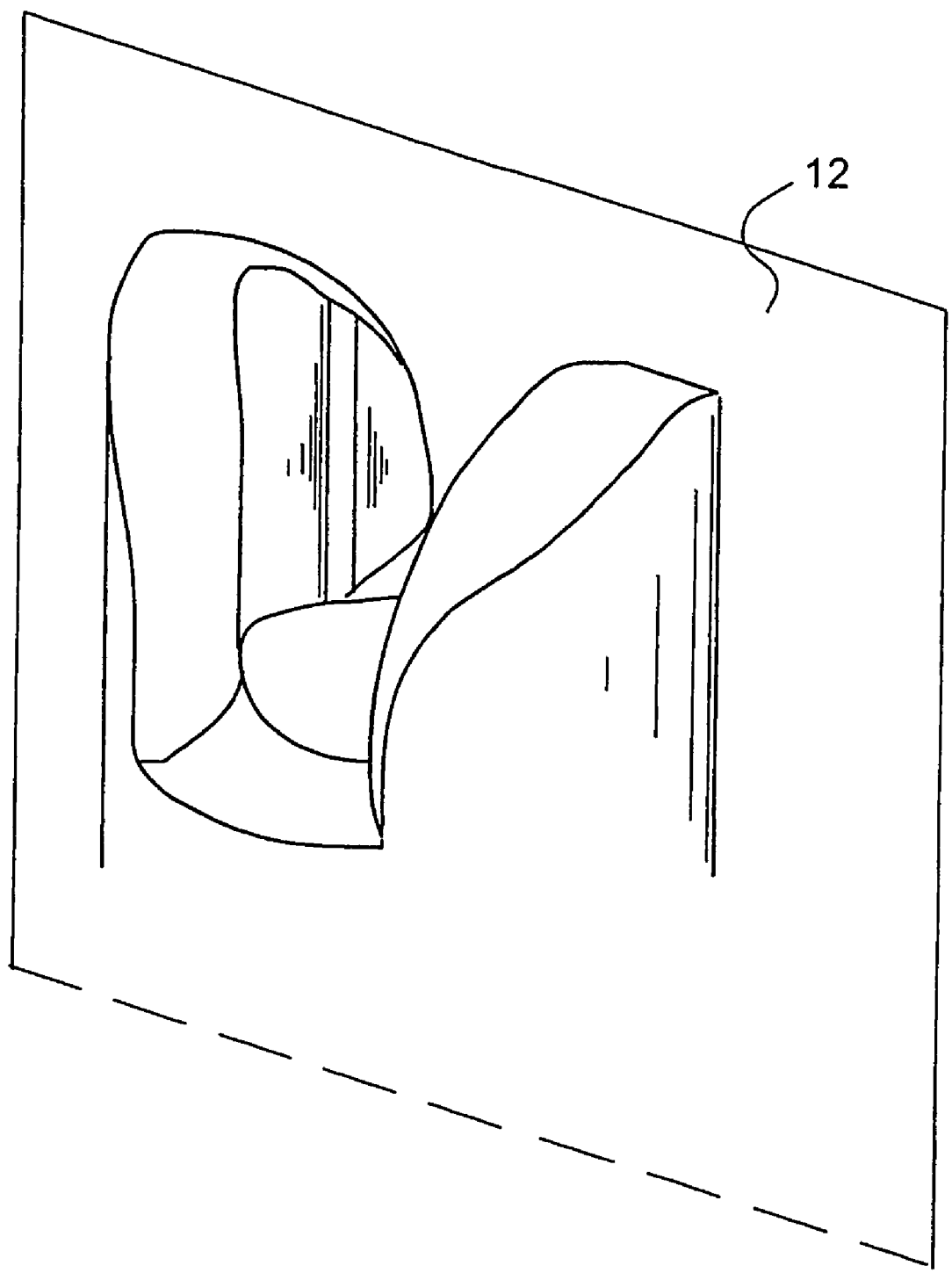

FIG. 5 also shows the tip structure of a plunger according to a third embodiment of the invention.

Figure 6:
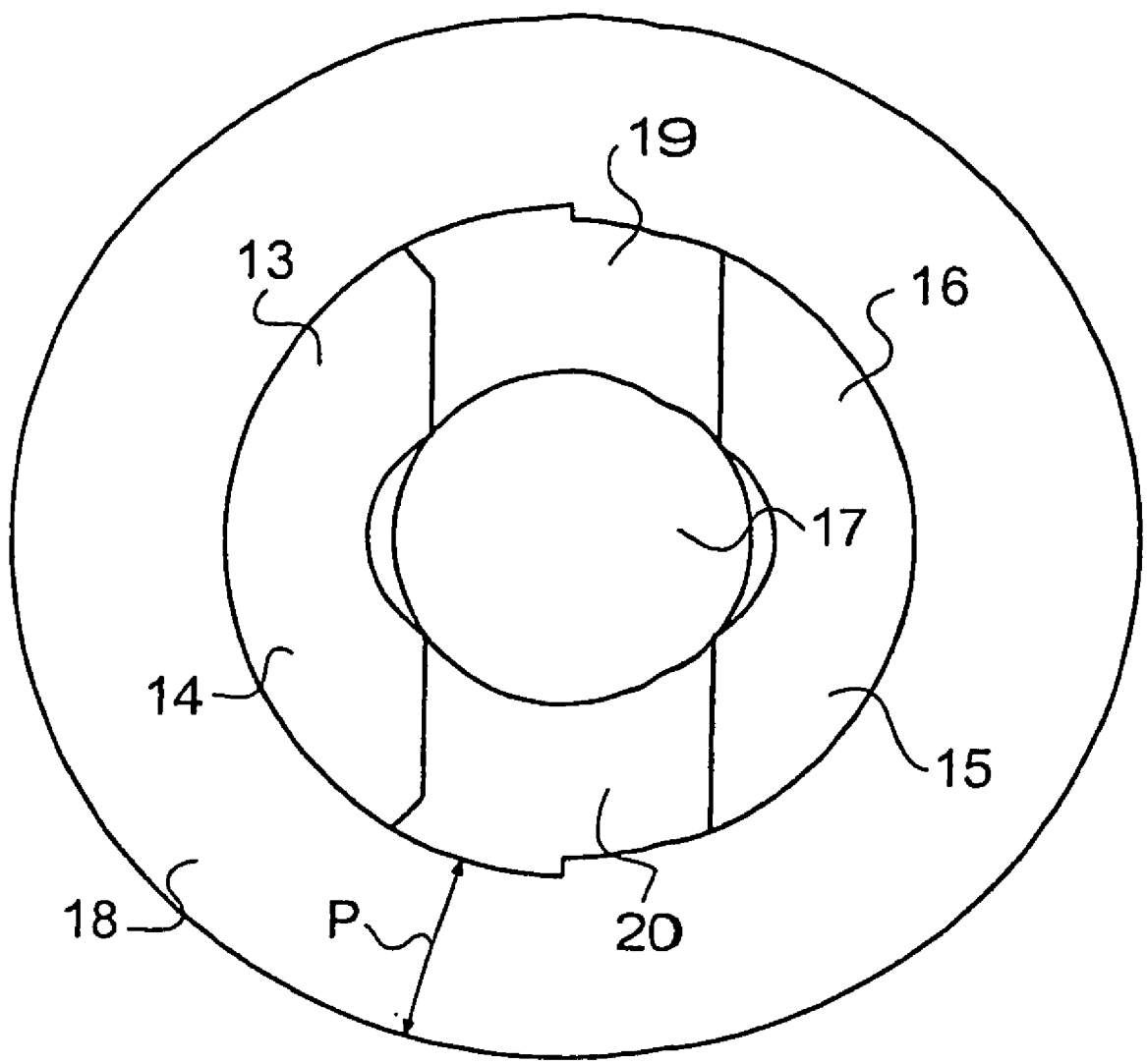

FIG. 6 shows the tip structure of a plunger according to a fourth embodiment of the invention, as seen from the first end of the plunger.

Figure 7:
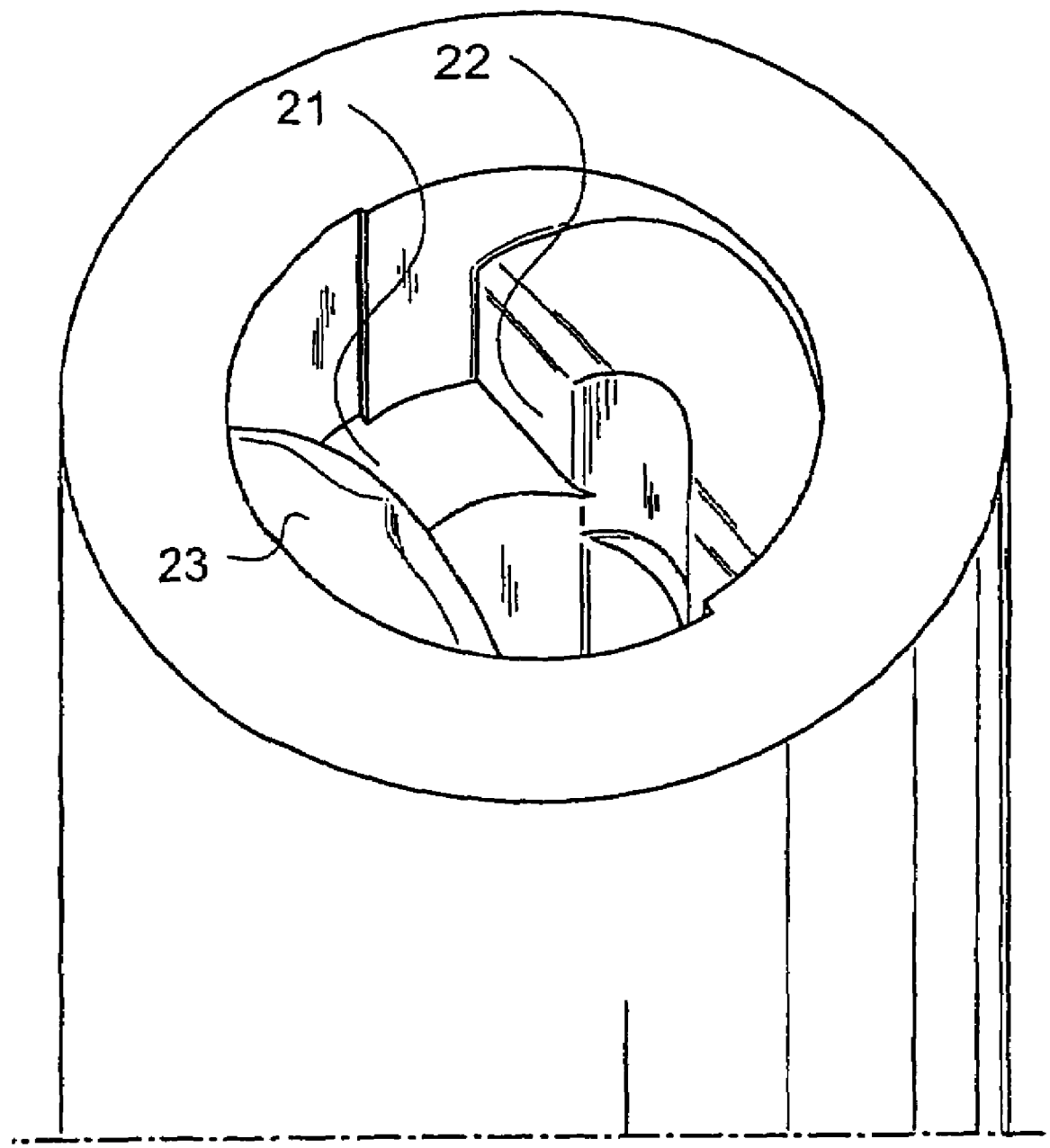

FIG. 7 shows the tip structure of a plunger according to a fifth embodiment of the invention.

DETAILED DESCRIPTION OF THE DRAWING

Figure 1:
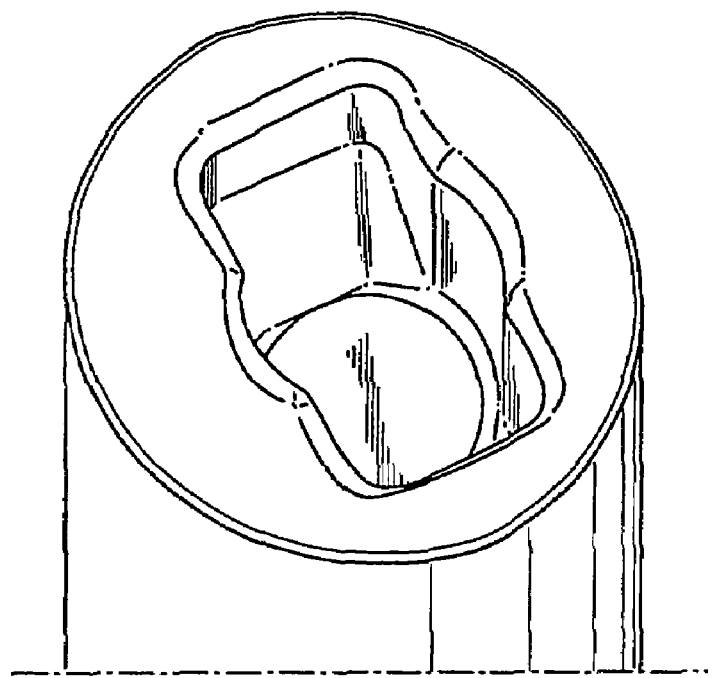
FIG. 1 shows the tip structure of a plunger of an inserter according to the prior art intended for the positioning of an intrauterine device.

FIG. 1 shows the tip structure of a plunger of an inserter according to the prior art intended for the positioning of an intrauterine device.

Figure 2:
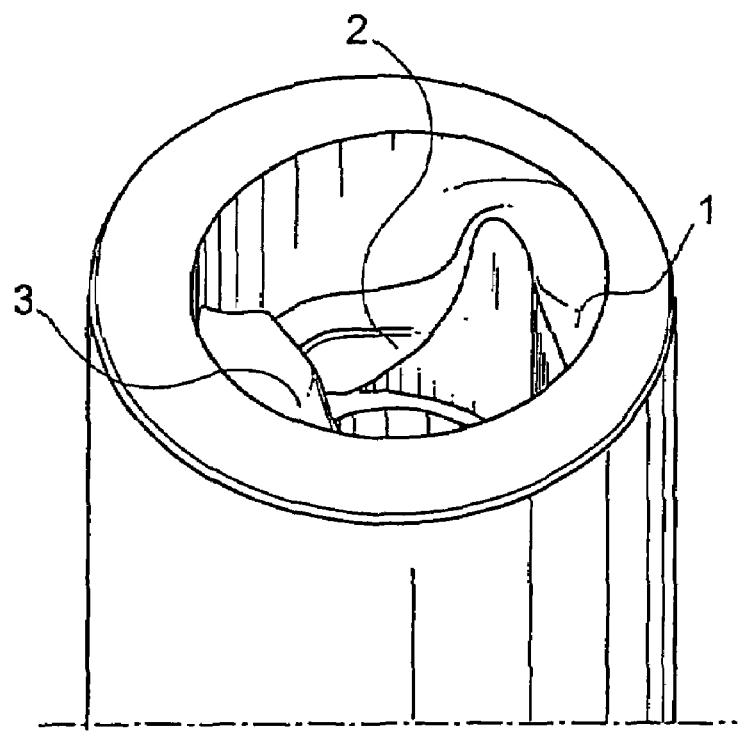
FIG. 2 shows the tip structure of a plunger according to a first embodiment of the invention.

FIG. 2 shows the tip structure of a plunger according to a first embodiment of the invention. The Figure shows three of the four surfaces, i.e. the surfaces 1, 2 and 3, of which the surfaces 1 and 2 form a surface pair, and the surface 3 forms a surface pair with the fourth surface. In this embodiment the surface pairs are connected with each other.

Figure 3:
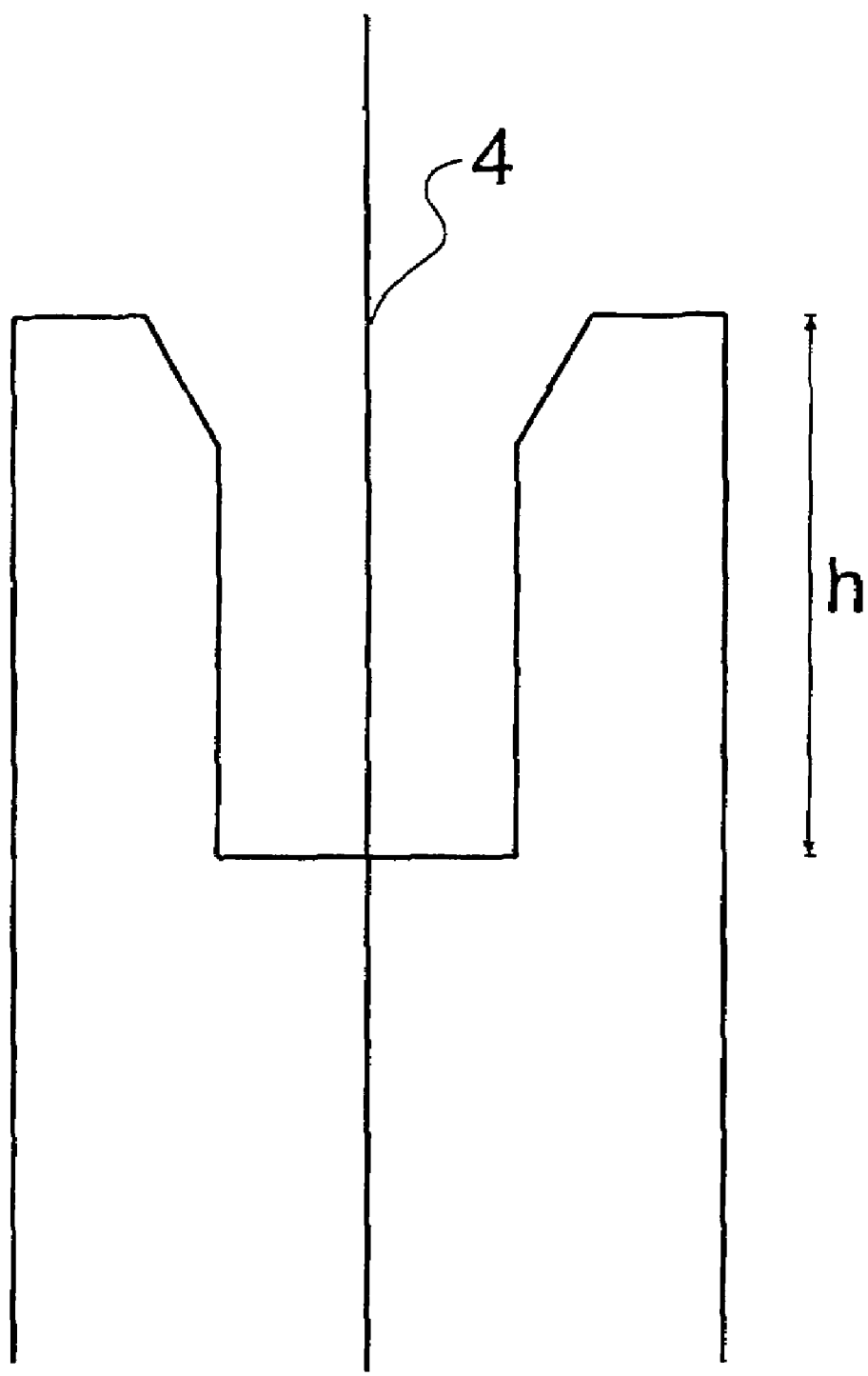
FIG. 3 shows the longitudinal cross-section of the tip structure of a plunger according to a second embodiment of the invention.

FIG. 3 shows the longitudinal cross-section of the tip structure of a plunger according to a second embodiment of the invention. The cross-section is taken along the longitudinal axis 4. The Figure shows that the surface pairs are mirror images of each other in relation to a first plane in parallel with the longitudinal axis 4, which in this case is the plane, which is perpendicular to the surface of the paper. The Figure further shows the length h of the tip portion.

Figure 4:
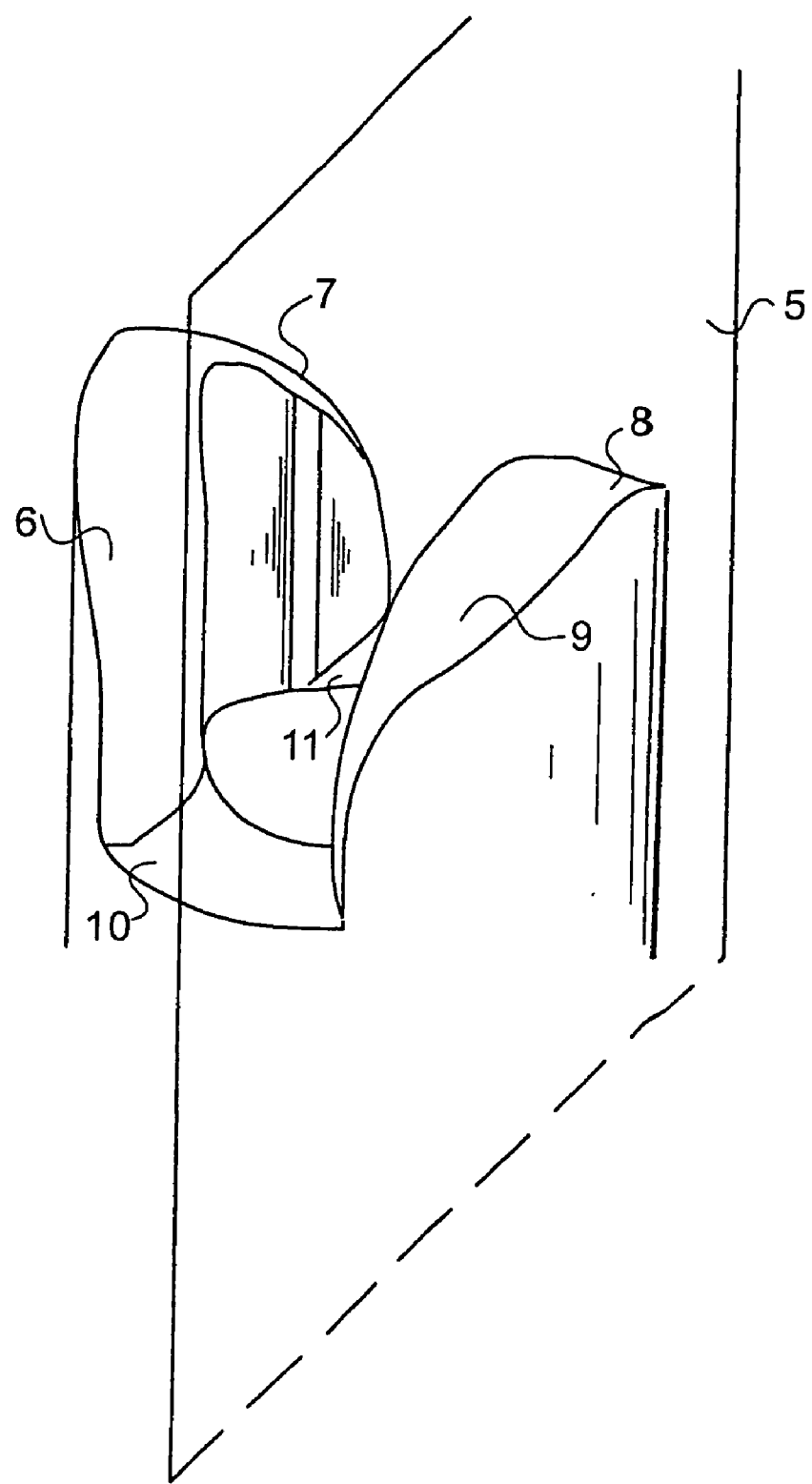
FIG. 4 shows the tip structure of a plunger according to a third embodiment of the invention.

FIGS. 4 and 5 show the tip structure of a plunger according to a third embodiment of the invention. The Figure shows the surfaces 6, 7, 8 and 9, of which the surfaces 6 and 7 form a first surface pair and the surfaces 8 and 9 form a second surface pair. In the presented embodiment all surfaces turn substantially 90° in relation to both said planes. In this embodiment the surfaces are not connected with each other, but surfaces 10 and 11 are left between the surface pairs, which surfaces 10 and 11 are substantially in parallel with the direction of the plane of the cross-section of the plunger.

FIG. 4 shows in addition the first plane 5 in parallel with said longitudinal axis, whereby the surface pairs are mirror images of each other in relation to this plane. FIG. 5 shows the tip of the plunger of the same embodiment as in FIG. 4, but FIG. 5 shows the plane 12 perpendicular to the first plane 5.

FIG. 6 shows the tip structure of a plunger according to a fourth embodiment of the invention, as seen from the first end of the plunger. The figure shows the surfaces 13, 14, 15 and 16 as well as the opening of the plunger 17. The Figure shows that the longitudinal axis of the opening is the same as the longitudinal axis of the plunger. The Figure shows also that the surface pair formed by the surfaces 13 and 14 is not a mirror image of the surface pair formed by the surfaces 15 and 16, but that the surfaces 13 and 14 turn less along the length of the top portion than the surfaces 15 and 16. In this embodiment the tip portion has further an outer shell 18, which has a substantially uniform wall thickness P along the whole length of the tip portion. The embodiment shown in FIG. 2 has also an outer shell like this.

The presented fourth embodiment has further surfaces 19 and 20 corresponding to those of the third embodiment (surfaces 10, 11) and these surfaces 19 and 20 are substantially in parallel with the direction of the plane of the cross-section of the plunger.

FIG. 7 shows the tip structure of a plunger according to a fifth embodiment of the invention. In this embodiment the tip structure has a surface 21, which is substantially in parallel with the direction of the cross section of the plunger, i.e. substantially in parallel with direction of the plunger end surface. In addition, the tip structure has adjacent to this surface 21 a surface 22, which at its lower edge is perpendicular to the surface 21 and later turns closer towards the direction of the plunger end surface. This creates thus one surface pair, which is symmetric in relation to the second plane. The other side of the tip structure is formed by the surface 23, which is arched. In this embodiment the other side of the tip structure directs and turns the inserter into the correct position, and the other side prevents a wrong position from being created and the inserter from being stuck in the tip structure.

The invention claimed is:

1. A plunger intended for an inserter for an intrauterine device with a T-body, wherein the plunger has
   a first end and a second end, and a first dimension, which is the longitudinal direction of the plunger, and the length of which plunger in its longitudinal direction is substantially larger than the diameter of the cross-section perpendicular to the longitudinal direction, and the cross-section of which plunger is substantially circular, and the plunger has an opening in its longitudinal direction such that the longitudinal axis of the opening is substantially the same as the longitudinal axis of the plunger, wherein the opening is at the first end of the plunger and expands in a direction perpendicular to the direction of the longitudinal axis to define a tip portion, so that the tip portion has at least one surface, which along at least a portion of the length of the tip portion turns at least 35° in relation to a first plane in parallel with the longitudinal axis, wherein said at least one surface turns also at least 35° in relation to a plane that is perpendicular to said direction of the longitudinal axis, along at least a portion of the length of the tip portion, such that said at least one surface will turn an intrauterine device having a T-body from an incorrect position into a correct position for positioning said intrauterine device within said plunger as the intrauterine device is being retracted into position within said plunger.

2. A plunger according to claim 1, wherein the tip portion has two surfaces.

3. A plunger according to claim 2, wherein said two surfaces form a surface pair.

4. A plunger according to claim 3, wherein the surfaces forming the surface pair of said surface pair are mirror images of each other in relation to a second plane in parallel with the longitudinal axis, whereby this second plane is perpendicular to said first plane.

5. A plunger according to claim 1, wherein the tip portion has four surfaces.

6. A plunger according to claim 5, wherein said four surfaces form two surface pairs, which are mirror images of each other in relation to said first plane in parallel with the longitudinal axis.

7. A plunger according to claim 6, wherein said surface pairs are connected with each other.

8. A plunger according to claim 6, wherein in at least one surface pair the surfaces forming the surface pair are mirror images of each other in relation to a second plane in parallel with the longitudinal axis, whereby the second plane is perpendicular to said first plane.

9. A plunger according to claim 1, wherein it has in addition at least one surface, which is substantially in parallel with said first plane.

10. A plunger according to claim 1, wherein said at least one surface turns 90° in relation to the first plane and 90° in relation to the plane that is perpendicular to said direction of the longitudinal axis.

* * * * *

UNITED STATES PATENT AND TRADEMARK OFFICE
CERTIFICATE OF CORRECTION

PATENT NO.        : 7,661,429 B2
APPLICATION NO.   : 10/579207
DATED             : February 16, 2010
INVENTOR(S)       : Ilkka Jutila It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 682 days.

Signed and Sealed this

Thirtieth Day of November, 2010

David J. Kappos
*Director of the United States Patent and Trademark Office*